United States Patent [19]

Reynes et al.

[11] Patent Number: 4,632,986

[45] Date of Patent: Dec. 30, 1986

[54] PROCESS FOR PURIFYING THIOCARBAMYLSULFENAMIDES

[75] Inventors: Enrique G. Reynes, Middleburg Heights; John O. Leising, Avon Lake, both of Ohio

[73] Assignee: The BFGoodrich Company, Akron, Ohio

[21] Appl. No.: 760,225

[22] Filed: Jul. 29, 1985

[51] Int. Cl.$^4$ .................... C07C 155/02; C07D 265/30
[52] U.S. Cl. ...................................... 544/85; 540/480; 540/481; 540/596; 540/597; 540/598; 540/602; 544/130; 544/141; 544/160; 546/189; 546/190; 546/208; 546/226; 546/230; 546/233; 546/245; 546/247; 548/523; 548/531; 548/542; 558/390; 558/392; 558/394; 558/430; 558/432; 558/433; 558/436; 564/75

[58] Field of Search ........... 260/239 BF, 243.3, 244.4, 260/245.7, 464, 465 E, 465.5 R; 544/85, 130, 141, 160; 546/189, 190, 208, 226, 230, 233, 245, 247; 548/523, 531, 542; 564/75; 558/390, 392, 394, 430, 432, 433, 436

[56] References Cited

U.S. PATENT DOCUMENTS

| | | | |
|---|---|---|---|
| 3,904,686 | 9/1975 | Arnold et al. | 564/75 |
| 3,985,743 | 10/1976 | Taylor | 544/85 X |
| 4,006,251 | 2/1977 | Taylor et al. | 564/75 X |

Primary Examiner—Richard L. Raymond
Attorney, Agent, or Firm—J. Hughes Powell, Jr.; Alan A. Csontos

[57] ABSTRACT

Thiocarbamylsulfenamides are readily recovered from solutions of the thiocarbamylsulfenamides by the addition of a dilute aqueous caustic solution, to flash off the solvent separating the thiocarbamylsulfenamide from the resulting water slurry and drying the thiocarbamylsulfenamide.

6 Claims, No Drawings

PROCESS FOR PURIFYING THIOCARBAMYLSULFENAMIDES

BACKGROUND OF THE INVENTION

Methods for preparing thiocarbamylsulfenamide accelerators are described in U.S. Pat. No. 3,985,743. In one method an amine in a solvent is reacted with a bleach solution and carbon disulfide. At the end of the reaction, the water phase is separated from the organic phase containing the thiocarbamylsulfenamide reaction product. The organic phase is then washed with water. The solvent is removed as by flashing, distillation and the like and the remaining thiocarbamylsulfenamide reaction product is washed with a solvent such as an alcohol, centrifuged or filtered and dried.

It is desirable to eliminate some of these steps, especially the use of an expensive solvent that must be recovered and cleaned up before reuse, requiring expensive equipment and utilities as in processing steps, i.e., washing, filtration, drying, solvent recovery and purification and the like. Of equal importance is obtaining a thiocarbamylsulfenamide reaction product having better storage stability.

Thiocarbamylsulfenamides, N,N'-[thiocarbonylthio]-dimorpholine, for example, are normally not very storage stable, particularly under high temperature storage conditions that are often encountered under summer conditions, or when exposed to other sources of heat. Under such conditions the thiocarbamylsulfenamide suffers degradation and a loss in activity. This results in slower cure rates and a decrease in scorch time. An incomplex process for preparing more stable thiocarbamylsulfenamides is desired.

SUMMARY OF THE INVENTION

Thiocarbamylsulfenamides are readily recovered from solutions of the thiocarbamylsulfenamides by the addition of a dilute aqueous caustic solution, to flash off the solvent, separating the thiocarbamylsulfenamide from the resulting water slurry, and drying the thiocarbamylsulfenamide.

DETAILED DESCRIPTION

To obtain the advantages of the invention, a critical combination of features must be observed; the amount of caustic used, where and how it is introduced, the stripping temperature, and optionally cooling the stripped slurry in order to keep the thiocarbamylsulfenamide stable.

The caustic used may be sodium hydroxide, potassium hydroxide, lithium hydroxide, calcium hydroxide, magnesium hydroxide, barium hydroxide, sodium carbonate and the like. However, sodium hydroxide is generally used. The caustic is used in dilute aqueous solutions for example ranging from about 0.2 to about 2 percent, more preferably from 0.7 to 0.9 percent in water. The amount of caustic used is from about 0.2±0.025 equivalent per mol of thiocarbamylsulfenamide is normally used. Lower levels as 0.005 do not produce stable products, amounts as much as 0.5 can cause degradation and loss of yield of the thiocarbamylsulfenamide.

It is essential that the caustic solution be added to the organic phase, i.e., the solvent containing the thiocarbamylsulfenamide. The temperature of the caustic solution should be from about 30° to about 90° C., more preferably about 50° to 90° C. The temperature of the organic phase should be at about 35° to 80° C. In other words, enough caustic at a temperature from about 30° to 90° C. should be added to the organic phase so that the temperature of the mixture of acid and organic phase is at about the boiling point of the solution, about 35° to 80° C. In other words, if the solvent is methylene chloride and the organic phase is below 35° C., the temperature of the caustic solution should be high enough to raise the mixture temperature to about 35° to 40° C., and vice versa. At temperatures substantially greater than the 50° C. solvent boiling point with methylene chloride undesirable side reactions can occur during the stripping operation that will have an adverse effect on the thiocarbamylsulfenamides, resulting in lower purity, and a less stable and active product. At lower temperatures, below the solvent boiling point, more expensive vacuum stripping would be required, and while this is satisfactory, a less expensive process is had when the defined parameters are observed, requiring less expensive equipment and utility costs.

In this method, as the solvent is removed, the impurities that are solvent soluble are concentrated in the remaining solvent and an oil in water emulsion is formed with the aqueous caustic solution which enhances reaction of the caustic with the impurities, converting them into a water soluble form so that they are readily removed by washing with water. If the reverse procedure is followed, that is, the organic phase is added to the aqueous caustic solution, the oil in water emulsion formed has a short life, the solvent flashes off leaving the impurities behind as a precipitate in the product, rather than dissolved in water in accordance with the process of this invention, resulting in lower purity, less stable thiocarbamylsulfenamide.

An optional and preferred feature of the process is cooling the slurry to 20° to 40° C. immediately following the flashing operation, preferably to about 30°±50° C. At this temperature the slurry may be held for at least 8 hours without further processing. Otherwise the slurry would have to be processed at once to prevent degradation of the thiocarbamylsulfenamide. This lead time allows flexibility in operations. The thiocarbamylsulfenamide is then isolated from the water slurry by any conventional method, filtering, centrifuging and the like, and dried in vacuum or air.

This novel and improved process is especially useful with thiocarbamylsulfenamides generally. The process is particularly applicable to thiocarbamylsulfenamides prepared as described in U.S. Pat. No. 3,985,743 wherein an amine and a monohaloamine were reacted with carbon disulfide in the presence of a base. The thiocarbamylsulfenamides preprepared by the process of this patent have the formula

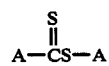

wherein A is selected from the group consisting of

and mixtures thereof, where $R_a$ and $R_b$ are selected from the group consisting of hydrogen, an alkyl radical containing 1 to 24 carbon atoms, a cyanoalkyl radical containing 2 to 12 carbon atoms, an alkoxyalkyl radical containing 2 to 12 carbon atoms, an alkenyl radical containing 2 to 18 carbon atoms, all wherein the alkyl structure can contain secondary or tertiary carbon atom structures; a cycloalkyl radical containing 4 to 8 carbon atoms in the ring and additionally may have 1 to 4 carbon atoms alkyl substituents thereon; phenyl; an alkaryl or aralkyl radical containing 7 to 18 carbon atoms in the radical; and where R is hydrogen or an alkyl radical containing 1 to 2 carbon atoms and x=4 to 7.

Examples of such compounds are thiocarbamylsulfenamide and the derivatives thereof such as N,N-dimethyl thiocarbamylsulfenamide; N-methyl-N'-ethyl thiocarbamylsulfenamide; N,N,N',N'-tetramethyl thiocarbamylsulfenamide; N,N,N',N'-tetraethyl thiocarbamylsulfenamide; amide; N,N,N',N'-tetrabutyl thiocarbamylsulfenamide; N-methyl-N',N'-diisopropyl thiocarbamylsulfenamide; N-octyl-N'-butyl thiocarbamylsulfenamide; N,N-didodecyl thiocarbamylsulfenamide; N,N-dioctadecyl thiocarbamylsulfenamide; N-isopropyl-N',N'-dicyclobutyl thiocarbamylsulfenamide; N-methyl-N-phenyl-N',N'-dimethyl carbamylsulfenamide; N,N-dimethyl-N'-tetramethylene thiocarbamylsulfenamide; N,N-dimethyl-N'-tetramethylene carbamylsulfenamide; N'-oxydiethylene thiocarbamylsulfenamide; N,N-dimethyl-N'-oxydiethylene thiocarbamylsulfenamide; N,N-di-(α-cyanopropyl)thiocarbamylsulfenamide; N,N,N',N'-tetramethoxyethyl thiocarbamylsulfenamide; N,N-diallyl-N',N'-dimethyl thiocarbamylsulfenamide; N,N-dicyclohexyl-N'-N'-dibutyl thiocarbamylsulfenamide; N-cyclooctyl-N',N'-(1,3-dimethylhexyl)thiocarbamylsulfenamide; N-benzyl-N',N'-diethyl thiocarbamylsulfenamide; N-pentamethylene-N',N'-dipropyl thiocarbamylsulfenamide; N,N'-di-(tetramethylene)thiocarbamylsulfenamide; N,N'-di-(hexamethylene)thiocarbamylsulfenamide; N-pentamethylene-N'-oxydiethylene thiocarbamylsulfenamide; N-heptamethylene-N'-oxydiethylene thiocarbamylsulfenamide; N,N-di-(oxydiethylene)thiocarbamylsulfenamide; N-oxydiethylene-N'-2,6-dimethyloxydiethylene thiocarbamylsulfenamide; N,N'-di-(2,6-dimethyloxydiethylene)thiocarbamylsulfenamide; and N-2,6-dimethyloxydiethylene-N'-ethyl thiocarbamylsulfenamide.

The monohaloamines have the formula X—A, wherein X is —Cl, —Br, or —I, and A is defined as above. Examples of monohaloamines are monochloroamine, monobromoamine, methyl-chloroamine, ethyl-chloroamine, ethyl iodoamine, t-butyl-chloroamine, hexyl-chloroamine, dodecyl-chloroamine, dimethyl-chloroamine, dimethyl-bromoamine, diethyl-chloroamine, ethyl-propyl-chloroamine, diisopropyl-chloroamine, ethyl-hexyl-chloroamine, dioctyl-chloroamine, dioctyl-bromoamine, didodecyl-chloroamine, dioctadecyl-chloroamine, diallyl-chloroamine, α-cyanopropyl-chloroamine, di-methoxyethylchloroamine, phenyl-chloroamine, benzyl-chloroamine, benzyl-bromoamine, 3,5-diethylbenzyl-chloroamine, cyclopentyl-chloroamine, cyclohexyl-chloroamine, dicyclobutyl-chloroamine, dicyclohexyl-bromamine, tetramethyleneamine chloride, heptamethyleneamine chloride, hexamethyleneamine chloride, hexamethyleneamine iodide, 4-methyl-hexamethyleneamine chloride, oxydiethyleneamine chloride, 2,6-dimethyloxydiethyleneamine chloride, and the like.

The monochloroamines are preferred. They are readily prepared by reacting a primary or secondary amine with a chlorinating agent such as sodium hypochlorite, NaOCl. This can be done in situ prior to the reaction of the amine and the chloroamine with the carbon disulfide. Though all reference in the specification will be made to monochloroamines as used in the process, it is understood that the monobromoamines and monoiodoamines may also be used.

Even more preferred are those monochloroamines wherein when A is —$NR_aR_b$, $R_a$ is hydrogen or the same as $R_b$, and $R_b$ is an alkyl radical containing 1 to 24 carbon atoms or a cycloalkyl radical containing 4 to 8 carbon atoms in the ring, and when A is

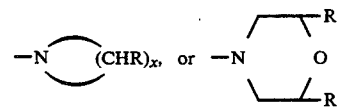

x is 4 to 7, and R is hydrogen or a methyl radical. Examples of such compounds are methyl-chloroamine, ethyl-chloroamine, t-butyl-chloroamine, hexyl-chloroamine, dimethyl-chloroamine, diethyl-chloroamine, ethyl-propyl-chloroamine, diisopropyl-chloroamine, disecbutyl-chloroamine, dihexyl-chloroamine, hexyl-octyl-chloroamine, diisooctyl-chloroamine, didecyl-chloroamine, methyl-dodecyl-chloroamine, ditetradecyl-chloroamine, dioctadecyl-chloroamine, cyclobutyl-chloroamine, cyclohexyl-chloroamine, dicyclopentyl-chloroamine, dicyclohexylchloroamine, di-(4-methylcyclohexyl)-chloroamine, tetramethyleneamine-chloroamine, pentamethyleneamine-chloride, 2,6-dimethyloxydiethyleneamine chloride, and the like.

The amines have the formula H—A, wherein A is defined as above. Examples of such amines would be those broadly disclosed haloamines as listed above except for the replacement of the chlorine atom with a hydrogen atom. More preferred are those amines wherein, when A is —$NR_aR_b$ is hydrogen or the same as $R_b$ and $R_b$ is an alkyl radical containing 1 to 24 carbon atoms; and when A is

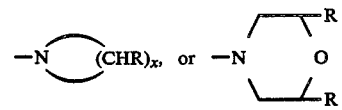

wherein x=4 to 7, and R is hydrogen or a methyl radical. Examples of the more preferred amines are methylamine, ethylamine, n-butylamine, hexylamine, dodecylamine, dimethylamine, diethylamine, ethylpropylamine, dibutylamine, dihexylamine, dioctylamine, didoceylamine, dioactadecylamine, tetramethylamine, pentamethylamine, hexamethyleneamine, oxydiethyleneamine, 2,6-dimethyloxydiethyleneamine, and the like.

The base can be an alkali metal hydroxide such as sodium hydroxide, potassium hydroxide, and the like; an alkali metal alcoholate wherein the alcohol is an aliphatic alcohol containing 1 to 10 carbon atoms such as sodium methoxide, sodium ethoxide, potassium butoxide, and the like; or the allkali metal salt of a weak acid such as organic acids containing 1 to about 8 carbon atoms including acetic acid, citric acid, benzoic acid and salicyclic acid; boric acid, phosphoric acid, carbonic acid, and the like. Examples of alkali metal salts of weak acids are sodium acetate, potassium benzoate, sodium borate, sodium phosphate, sodium carbonate, and the like. Excellent results were obtained when using an alkali metal hyroxide such as sodium hydroxide as the base.

The reactions can be conducted in a aqueous/non-aqeuous medium. To this manner, higher yields and more pure products can be obtained. The medium consists of water and an organic solvent, preferably a chlorinated organic solvent such as methylene chloride, carbon tetrachloride, chloroform, ethylenedichloride, 1,1,1-trichloroethane, 1,1,2-trichloroethane, chlorobenzene, 1,1,2-trichloro, trifluoroethane and the like. The monochloroamine, the carbon disulfide and the thiocarbamylsulfenamide are all soluble in the non-aqueous phase.

The temperature of the reactions ranges from near the freezing point of the mixture, about $-20°$ C., to near the boiling point of the mixture, about $80°$ to $100°$ C. A more preferred range is from about $-10°$ C. to about $40°$ C. Reaction times are from about 0.2 hours to about 2 hours.

The amine and the monochloroamine can both be used in a molar excess of the amount of the carbon disulfide present. However, yields of over 50% and in excess of 90% based on the theoretical yield are readily obtained using about 1 mol of monochloroamine and 1 mol of amine to every 1 mol of carbon disulfide present. By-products of the reaction are sodium chloride and water (if sodium hyroxide is used).

The reactions are conducted with agitation. The thiocarbamylsulfenamides are usually crystalline materials but some are liquids at room temperatures.

The process is of particular value in the preparation of N-oxydiethylenethiocarbamyl-N'-oxydiethylenesulfenamide prepared from morpholine dissolved in methylene chloride by reaction with an aqueous NaOCl solution and carbon disulfide.

To demonstrate the practice of the invention, a thiocarbamylsulfenamide, N-oxydiethylenethiocarbamyl-N'-oxydiethylenesulfenamide, was prepared by reacting a solution of morpholine, dissolved in methylene chloride, sequentially with a bleach, NaOCl, solution and carbon disulfide in the manner described in U.S. Pat. No. 3,985,743. At the end of the reaction, the water phase was separated from the organic phase and the organic phase methylene chloride solution containing the N-oxydiethylenethiocarbamyl-N'-oxydiethylenesulfenamide was washed with water. To 238.6 volumes of the methylene chloride solution at a temperature of about $30°$ C. there was added 337 volumes of a 0.81 percent solution of sodium hydroxide in water, at a temperature of about $50°$ C. in an amount to provide 0.20 mol of sodium hydroxide per mol of N-oxydiethylenethiocarbamyl-N'-oxydiethylenesulfenamide. The methylene chloride was flashed off at a temperature of $38°$ C. and a pressure of 12 psi, collected and condensed for recycle. The N-oxydiethylenethiocarbamyl-N'-oxydiethylenesulfenamide was present suspended as a slurry in the water phase which also contained the impurities as water soluble sodium salts. The N-oxydiethylenethiocarbamyl-N'-oxydiethylenesulfenamide was isolated from the water slurry by centrifuging, and was then dried.

The dried N-oxydiethylenethiocarbamyl-N'-oxydiethylenesulfenamide had an unaged melting point of $138.2°$ C. After air aging in an oven at $100°$ C. for 60 minutes, the melting point was found to be $137.8°$ C., for a $\Delta T$ of 0.4. A $\Delta T$ of greater than about 2 is considered to represent an unstable product and a $\Delta T$ of less than 1 represents an extremely stable product. The product yield was an excellent 93.4%. The product was found to contain only 0.68% of dimorpholine thiuram disulfide impurity. This is to be compared to a prior art process not involving the caustic stripping step, and wherein methylene chloride was flashed off and the residual N-oxydiethylenethiocarbamyl-N'-oxydiethylenesulfenamide was washed with methanol to remove the impurities. The dried product was found to contain about 4% dimorpholine thiuram disulfide.

We claim:

1. A method for recovering and purifying a thiocarbamylsulfenamide reaction product of an amine and a monohaloamine reacted with carbon disulfide from a solution thereof in an organic solvent, comprising adding to said solution an aqueous caustic selected from the group consisting of aqueous sodium hydroxide, potassium hydroxide, lithium hydroxide, calcium hydroxide, magnesium hydroxide, barium hydroxide and sodium carbonate, in concentrations from about 0.2 to about 2 percent in water, to provide about $0.02 \pm 0.25$ mol equivalents of caustic per mol of thiocarbamylsulfenamide, said caustic solution being at a temperature of about $30°$ to about $90°$ C., to flash off the solvent, separating the thiocarbamylsulfenamide present suspended in a slurry of the water phase from the water, and drying the thiocarbamylsulfenamide.

2. A method of claim 1 wherein the thiocarbamylsulfenamide is N-oxydiethylenethiocarbamyl-N'-oxydiethylenesulfenamide, the solvent is a chlorinated organic solvent, the temperature of the mixture of acid solution and organic solvent is at about the boiling point of the solvent, about $30°$ to $90°$ C., and the N-oxydiethylenethiocarbamyl-N'-oxydiethylenesulfenamide is separated from the water phase by centrifuging.

3. A method of claim 1 wherein the water slurry of N-oxydiethylenethiocarbamyl-N'-oxydiethylenesulfenamide is cooled to $25°$ to $30°$ C. immediately after the solvent is flashed off.

4. A method of claim 2 wherein the thiocarbamylsulfenamide is N-oxydiethylenethiocarbamyl-N'-oxydiethylenesulfenamide, the solvent is methylene chloride, the caustic is sodium hydroxide, the temperature is about $40°$ C., and the N-oxydiethylenesulfenamide is separated from the water phase by centrifuging.

5. A method of claim 2 wherein the water slurry of N-oxydiethylenethiocarbamyl-N'-oxydiethylenesulfenamide is cooled to about $25°–30°$ C. after the solvent is flashed off.

6. A method of claim 4 wherein the water slurry of N-oxydiethylenethiocarbamyl-N'-oxydiethylenesulfenamide is cooled to $25°$ to $30°$ C. immediately after the solvent is flashed off.

* * * * *

UNITED STATES PATENT AND TRADEMARK OFFICE
CERTIFICATE OF CORRECTION

PATENT NO. : 4,632,986

DATED : December 30, 1986

INVENTOR(S) : Enrique G. Reynes, John O. Leising

It is certified that error appears in the above-identified patent and that said Letters Patent is hereby corrected as shown below:

Column 6, line 52, "about 40°C., and the N-oxydiethylene-sulfenamide" should read -- about 40°C., and the N-oxydiethylenethiocarbamyl-N'-oxydiethylenesulfenamide --.

Signed and Sealed this

Thirty-first Day of May, 1988

Attest:

DONALD J. QUIGG

Attesting Officer

Commissioner of Patents and Trademarks